(12) United States Patent
Alotibi et al.

(10) Patent No.: US 12,357,725 B1
(45) Date of Patent: Jul. 15, 2025

(54) CLINICAL DRESSING LOADED WITH COFFEE EXTRACT

(71) Applicant: KING SAUD UNIVERSITY, Riyadh (SA)

(72) Inventors: Fatimah Olyan Alotibi, Riyadh (SA); Buthainah Khalid Al Sughair, Riyadh (SA); Raedah Ibraheam Alharbi, Riyadh (SA); Naiyf Sultan Helial Alaloi Alharbi, Riyadh (SA); Jamal Mohammed Ali Khaled, Riyadh (SA); Ahmed Saad Alobaidi, Riyadh (SA); Shine Moosa Kadaikunnan, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/679,420

(22) Filed: May 30, 2024

(51) Int. Cl.
  *A61L 26/00* (2006.01)
  *A61K 36/74* (2006.01)

(52) U.S. Cl.
  CPC ........ *A61L 26/0057* (2013.01); *A61K 36/742* (2024.05); *A61L 26/0066* (2013.01); *A61L 2300/406* (2013.01)

(58) Field of Classification Search
  None
  See application file for complete search history.

(56) References Cited

U.S. PATENT DOCUMENTS

| | | | |
|---|---|---|---|
| 9,074,305 | B2 | 7/2015 | Glenn et al. |
| 2017/0290778 | A1 | 10/2017 | Waugh |
| 2019/0105261 | A1 | 4/2019 | Waugh et al. |
| 2022/0331389 | A1 | 10/2022 | Nishimura |

FOREIGN PATENT DOCUMENTS

| | | | | |
|---|---|---|---|---|
| CN | 105169173 | A | * | 12/2015 |
| KR | 102396666 | B1 | | 5/2022 |
| WO | WO-2023204346 | A1 | * | 10/2023 ............... A23F 5/02 |

OTHER PUBLICATIONS

Humaryanto et al. , 2019, Exploring the Potential of Green Coffee Extract for Wound Healing Treatment IOP Conf. Series: Earth and Environmental Science, 391, 012057 doi:10.1088/1755-1315/391/1/012057.*
Yousefian et al., Antimicrobial Wound Dressings: A Concise Review for Clinicians, 2023, Antibiotics, 12: 1434.*
El-Wakil, N. A. et al., "Bacterial cellulose/phytochemical's extracts biocomposites for potential active wound dressings," Environ. Sci. Pollut. Res. Int. 26: pp. 26529-26541 (2019).
Yuwono, H. S., "The New Paradigm of Wound Management Using Coffee Powder," Journal of Surgery 2(2): pp. 25-29 (2014).
Rawangkan, et al., "Potential Antimicrobial Properties of Coffee Beans and Coffee By-Products Against Drug-Resistant Vibrio cholerae", Fronteirs, vol. 9, Apr. 2022.
Fardiaz, "Antimicrobial Activity of Coffee (Coffea robusta) Extract", ASEAN Food Journal, vol. 10, No. 3, 1995.
Eladli, et al., "Antibiotic-resistant Staphylococcus epidermidis isolated from patients and healthy students comparing with antibiotic-resistant bacteria isolated from pasteurized milk", Saudi Journal of Biological Sciences, vol. 26, pp. 1285-1290, 2019.
Dai, et al., "Plant Phenolics: Extraction, Analysis and Their Antioxidant and Anticancer Properties", Molecules, vol. 15, pp. 7313-7352, 2010.
Almeida, et al., "Antibacterial activity of coffee extracts and selected coffee chemical compounds against enterobacteria", J Agric Food Chem, vol. 54, No. 23, pp. 8738-8743, Nov. 2006.
Almanaa, et al., "The extreme drug resistance (XDR) *Staphylococcus aureus* strains among patients: A retrospective study", Saudi Journal of Biological Sciences, vol. 27, pp. 1985-1992, 2020.
Alharbi, et al., "Prevalence of *Escherichia coli* strains resistance to antibiotics in wound infections and raw milk", Saudi Journal of Biological Science, vol. 26, pp. 1557-1562, 2019.

* cited by examiner

*Primary Examiner* — Terry A McKelvey
*Assistant Examiner* — Catheryne Chen
(74) *Attorney, Agent, or Firm* — Nath, Goldberg & Meyer; Joshua B. Goldberg

(57) ABSTRACT

A method of making a supplemented wound dressing including preparing a coffee extract with or without cardamom and supplementing the wound dressing with the coffee extract is provided. The coffee beans may be Khulani coffee beans and they may be green coffee beans, lightly roasted coffee beans, or medium roasted coffee beans. The supplemented wound dressing prepared according to this method is effective to inhibit bacterial growth, particularly growth of methicillin-resistant *Staphylococcus aureus*.

9 Claims, 4 Drawing Sheets

CLINICAL DRESSING LOADED WITH COFFEE EXTRACT

BACKGROUND

Field

The disclosure of the present patent application relates to wound healing and particularly to a clinical dressing loaded with coffee extract.

Description of Related Art

Infectious diseases are one of the most important causes of health and pathological problems in the world. Studies have confirmed the presence of pathogens in human skin and that they are the source of many diseases. For example, in Saudi Arabia, *S. epidermidis* bacteria were isolated from the skin of patients and the skin of healthy people (Eladli, M. G., et al., 2019. Antibiotic-resistant *Staphylococcus epidermidis* was isolated from patients and healthy students to compare with antibiotic-resistant bacteria isolated from pasteurized milk. *Saudi journal of biological sciences*, 26(6), pp. 1285-1290). The spread of strains of antibiotic-resistant *Escherichia coli* bacteria has been proven in the wounds of patients in Saudi Arabia (Alharbi, N. S., et al. 2019). Prevalence of *Escherichia coli* strains resistance to antibiotics in wound infections and raw milk. *Saudi journal of biological sciences*, 26(7), pp. 1557-1562). In another study in Saudi Arabia, wounds were found to be the source of more than 40% of methicillin-resistant *Staphylococcus aureus* strains, known as MRSA (Almanaa, T.N., et al. 2020). The extreme drug resistance (XDR) *Staphylococcus aureus* strains among patients: A retrospective study. Saudi Journal of Biological Sciences, 27(8), pp. 1985-1992.).

Plant preparations have been used to treat microbial infections for many decades (Redo, M. C., et al. (1989) 'A review of some antimicrobial compounds isolated from medicinal plants reported in the literature 1978-1988', Phytotherapy Research, 3(4), pp. 117-125. doi:10.1002/ptr.2650030402.) due to their therapeutic properties and chemical composition, which contains natural antimicrobials.

The coffee drink is one of the most popular drinks in the world, and many studies have confirmed that the coffee drink has vital activity against a wide range of pathogenic microbes, for example, Rawangkan and others stated that by-products of coffee beans can inhibit drug-resistant *Vibrio cholera* bacteria. (Rawangkan, A., et al., 2022. Potential Antimicrobial Properties of Coffee Beans and Coffee By-Products Against Drug-Resistant *Vibrio cholerae*. Frontiers in nutrition, 9.) Phenolic compounds in general, caffeine, chlorogenic acid and trigonylene are some of the most famous compounds found in coffee (*Coffea arabica*), which has an inhibitory ability for microbes (Almeida, A. A. P. et al. (2006) 'Antibacterial activity of coffee extracts and selected coffee chemical compounds against enterobacteria', Journal of Agricultural and Food Chemistry, 54(23), pp. 8738-8743. doi:10.1021/jf0617317.; Dai, J. and Mumper, R. J. (2010) 'Plant phenolics: Extraction, analysis and their antioxidant and anticancer properties', Molecules, 15(10), pp. 7313-7352. doi:10.3390/molecules15107313.). It was also found that caffeine has the ability to inhibit the production of certain mycotoxins and that it is effective against many Gram-negative and Gram-positive bacteria (Fardiaz, S. (1995) 'Antimicrobial Activity of Coffee (*Coffea robusta*) Extract', ASEAN Food Journal, 10(3), pp. 103-106.). Furthermore, studies have shown that coffee extracts have a role in inhibiting the replication of DNA viruses.

There have been numerous attempts to strengthen surgical dressings with various materials that enhance their effectiveness, for example, in 2018, Ehterami and others supported surgical dressings with insulin-chitosan nanoparticles to support skin wound healing in animal models. (Ehterami, A., et al. 2018). In vitro and in vivo study of PCL/COLL wound dressing loaded with insulin-chitosan nanoparticles on cutaneous wound healing in rats model. *International journal of biological macromolecules*, 117, pp. 601-609.) Simões et al. (Simões, D., et al., 2018. Recent advances on antimicrobial wound dressing: A review. *European Journal of Pharmaceutics and Biopharmaceutics*, 127, pp. 130-141.) confirmed that the pathogenicity and mortality rate associated with skin and soft tissue infections is high and wound dressings reinforced with antimicrobial agents are a viable way to reduce the risk of colonization of wounds by pathogenic microbes and improve healing rates.

Thus, a clinical dressing loaded with coffee extract solving the aforementioned problems is desired.

SUMMARY

Wound pathogens are one of the serious health problems facing the world, including Saudi Arabia. This innovation aims to confront these microbes and inhibit their activity with a natural extract that is safe on the skin and on the human body generally. The aqueous extract of Saudi coffee roasted to different degrees and prepared in a manner appropriate to the method of preparing Saudi coffee proved to be effective in inhibiting methicillin-resistant *Staphylococcus aureus* (MRSA), and surgical dressings reinforced with coffee extract produced in this innovation are also effective against this pathogenic bacterium compared to those that were not supported by the Saudi coffee extract.

Raw green Khulani coffee beans (sometimes also referred to as Khawlani Coffee Beans) were obtained from a local farm in Viva, Jazan, Saudi Arabia. These coffee beans were roasted in two different grades and the traditional Saudi coffee preparation method was simulated in the laboratory and an aqueous extract was produced from each. The resulting extracts were tested and demonstrated a strong inhibitory efficacy against methicillin-resistant *Staphylococcus aureus* growth. Medicinal dressings were supplemented with the extract, left to dry, kept for a whole month, tested during that time and proved their ability to inhibit MRSA in the ideal growth environment for bacteria, which means that they will be more effective if used directly on human skin.

In an embodiment, a supplemented wound dressing may be made by a method including providing coffee beans, washing the coffee beans drying the coffee beans, grinding the coffee beans, mixing about 10 g of the coffee beans with about 100 mL sterile distilled water to obtain an aqueous solution, boiling the aqueous solution for about 15 minutes to obtain an extract, sterilizing the extract, providing a wound dressing, adding the sterilized extract to a wound contacting portion of the wound dressing, and drying the wound dressing under sterile conditions to obtain the supplemented wound dressing.

In an embodiment, supplemented wound dressing prepared according to the present methods may be effective to inhibit bacterial growth, and in a particularly desirable embodiment the supplemented wound dressing prepared according to the present methods may be effective to inhibit the growth of *Staphylococcus aureus* when applied to the surface of a wound on a subject in need thereof.

In an embodiment, methods of preventing bacterial growth in a subject in need thereof are provided, including preparing a supplemented wound dressing according to the present methods and applying the supplemented wound dressing to a wound on the subject in need thereof. The supplemented wound dressing may inhibit bacterial growth in the wound on the subject in need thereof, including particularly inhibiting the growth of methicillin-resistant *Staphylococcus aureus*.

These and other features of the present subject matter will become readily apparent upon further review of the following specification.

BRIEF DESCRIPTION OF DRAWINGS

FIG. 4A shows an absence of MRSA inhibition by the unsupplemented dressing. FIG. 4B shows MRSA inhibition by a wound dressing supplemented with 100 microliters of medium roasted coffee extract without cardamom.

Similar reference characters denote corresponding features consistently throughout the attached drawings.

DETAILED DESCRIPTION

Figure 1:
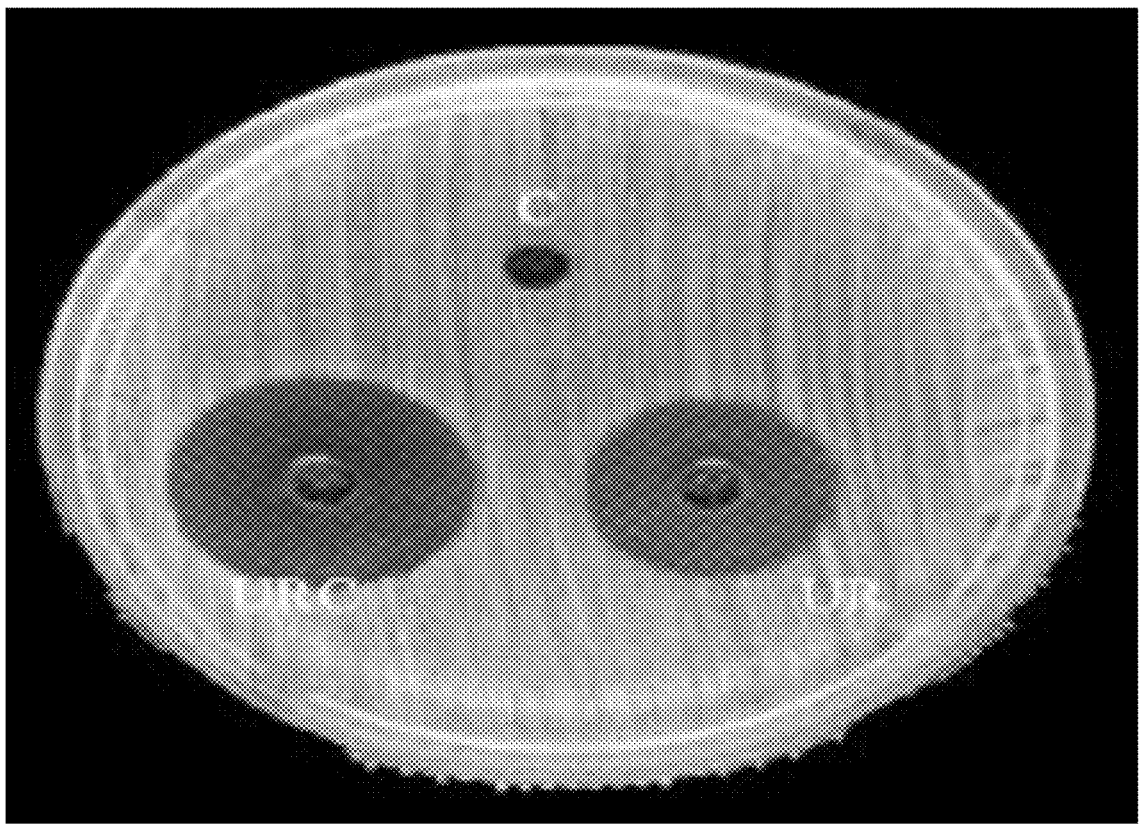
FIG. 1 shows the inhibition of MRSA growth resulting from 40 mg/mL of the aqueous extract of unroasted Saudi Khulani coffee beans as compared to unroasted Saudi Khulani coffee beans with cardamom. Physiological saline solution (0.89% sodium chloride) was also tested as a control sample. The transparent area around the wells to which the extract was added indicates inhibition of the growth of the tested bacteria.
Figure 2:
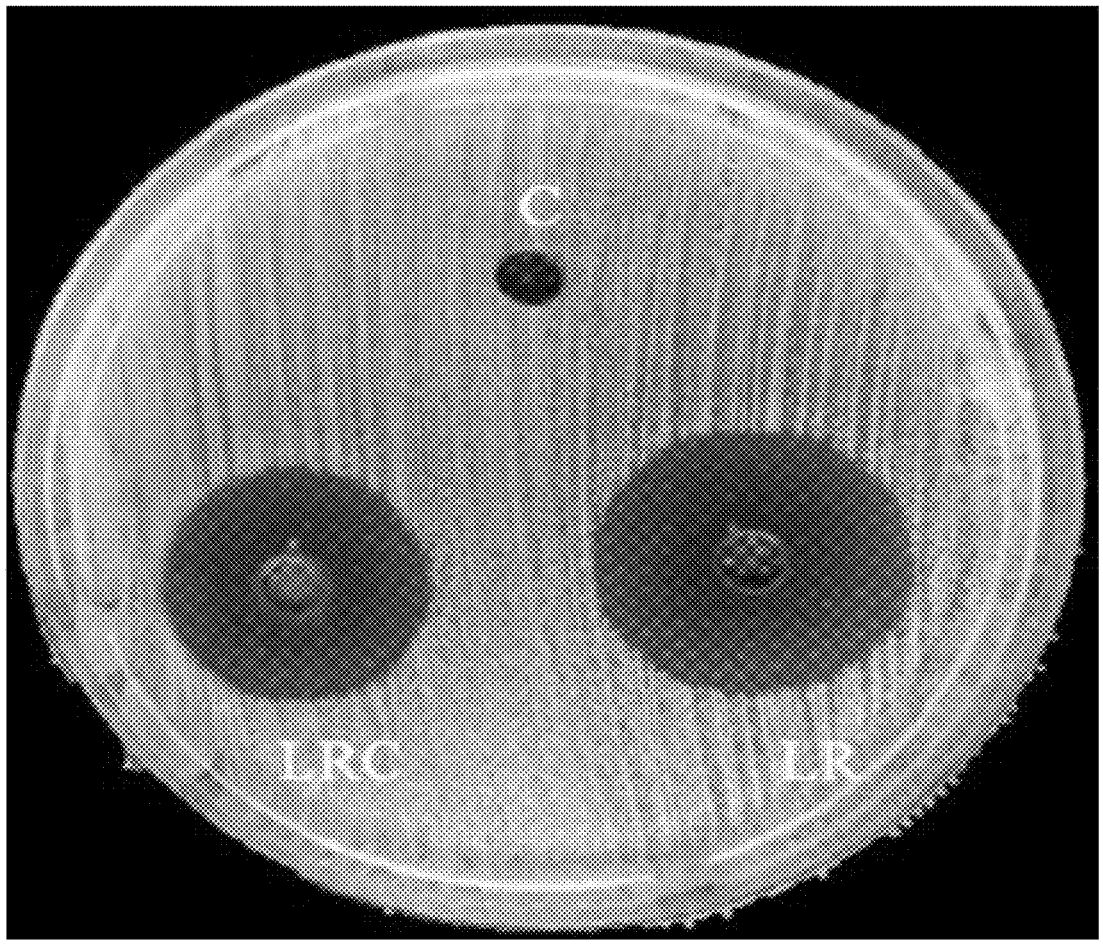
FIG. 2 shows the inhibition of MRSA growth resulting from 40 mg/mL of aqueous extract of lightly roasted Saudi Khulani coffee beans, either with or without cardamom, and physiological saline solution (0.89% sodium chloride) as a control sample. The transparent area around the pits to which the extract was added indicates inhibition of the growth of the tested bacteria.
Figure 3:
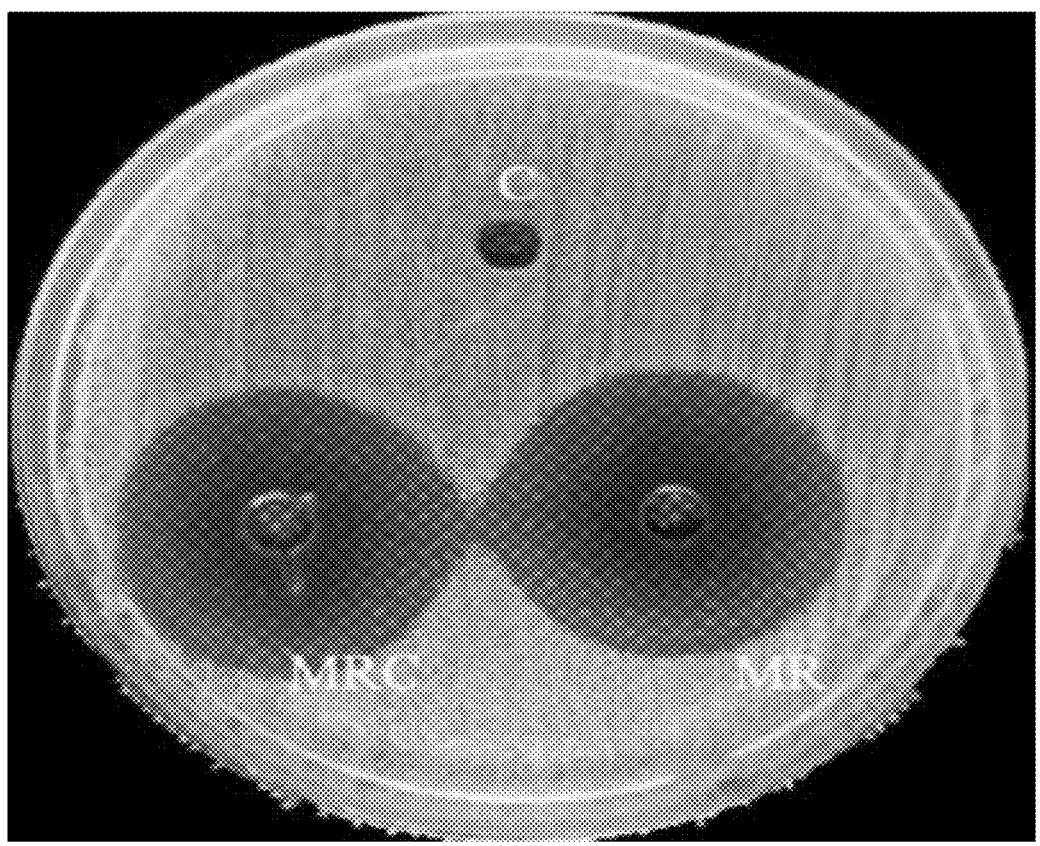
FIG. 3 shows the inhibition of MRSA growth resulting from 40 mg/mL of the aqueous extract of the toasted Saudi Khulani coffee beans with the addition of cardamom and non-cardamom and physiological saline solution (0.89% sodium chloride) as a control sample. The transparent area around the pits to which the extract was added indicates inhibition of the growth of the tested bacteria.
Figure 4A:
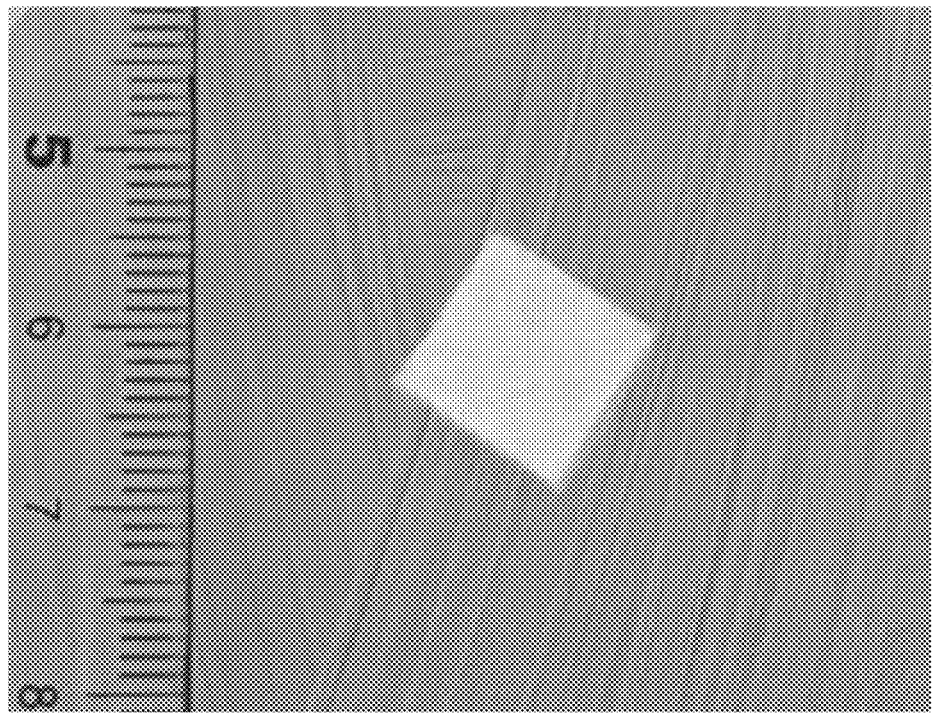
FIGS. 4A and 4B show the inhibition of MRSA growth resulting from the reinforcement of a wound dressing with 100 microliters of aqueous extract of medium-roasted Saudi Khulani coffee beans without the addition of cardamom. The transparent area around the pits to which the extract was added indicates inhibition of the growth of the tested bacteria.
Figure 4B:
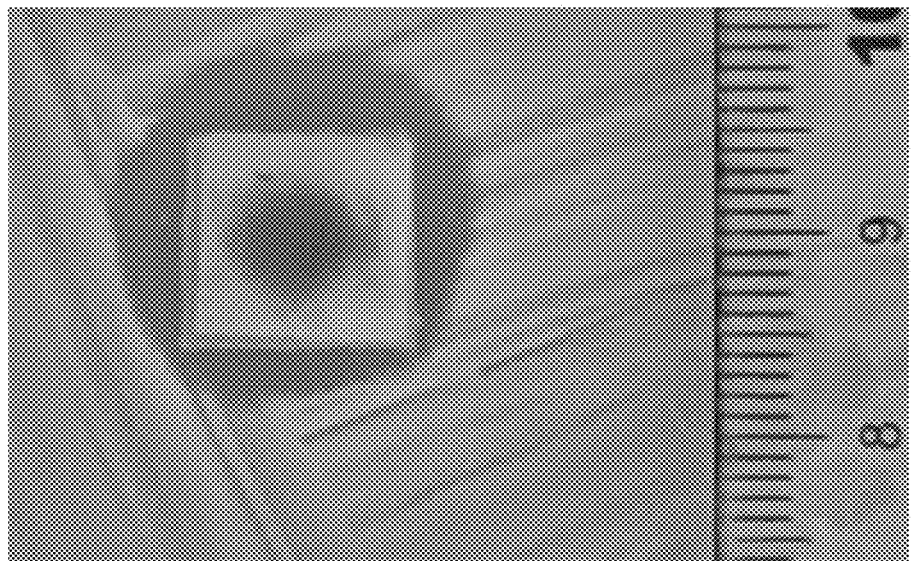

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

As used herein, "Kuhlani Coffee Beans" refers to a type of coffee bean cultivated in the Khawlan mountains in southwestern Saudi Arabia. These coffee beans may also be commonly referred to "Khawlani Coffee Beans".

As used herein, "wound dressing" refers to any bandage, wrap, covering, or other device now known or developed in the future to be placed on a wound and assist in the wound healing process.

Raw green Khulani coffee beans (sometimes also referred to as Khawlani Coffee Beans) were obtained from a local farm in Viva, Jazan, Saudi Arabia. These coffee beans were roasted in two different grades and the traditional Saudi coffee preparation method was simulated in the laboratory and an aqueous extract was produced from each. The resulting extracts were tested and demonstrated a strong inhibitory efficacy against methicillin-resistant *Staphylococcus aureus* growth. Medicinal dressings were supplemented with the extract, left to dry, kept for a whole month, tested during that time and proved their ability to inhibit MRSA in the ideal growth environment for bacteria, which means that they will be more effective if used directly on human skin.

In an embodiment, a supplemented wound dressing may be made by a method including providing coffee beans, washing the coffee beans drying the coffee beans, grinding the coffee beans, mixing about 10 g of the coffee beans with about 100 mL sterile distilled water to obtain an aqueous solution, boiling the aqueous solution for about 15 minutes to obtain an extract, sterilizing the extract, providing a wound dressing, adding the sterilized extract to a wound contacting portion of the wound dressing, and drying the wound dressing under sterile conditions to obtain the supplemented wound dressing.

In an embodiment, the coffee beans may be Khulani coffee beans. In a further embodiment, the Khulani coffee beans may have been grown in the Jizan region of Saudi Arabia.

In an embodiment, the coffee beans may be roasted prior to grinding. The coffee beans may be roasted at a temperature between about 190° C. and about 230° C. and for a period of between about 15 and about 30 minutes. In a particular embodiment, the coffee beans may be roasted at a temperature of about 190° C., and for about 15 minutes. In a further embodiment, the coffee beans may be roasted at a temperature of about 230° C., and for about 30 minutes. In an alternative embodiment, the coffee beans may not be roasted (sometimes referred to as using "green coffee beans").

In an embodiment, cardamom may be added to the aqueous solution prior to boiling. In some embodiments, about 2 g of cardamom may be added to the aqueous solution prior to boiling.

In an embodiment, supplemented wound dressing prepared according to the present methods may be effective to inhibit bacterial growth, and in a particularly desirable embodiment the supplemented wound dressing prepared according to the present methods may be effective to inhibit the growth of *Staphylococcus aureus* when applied to the surface of a wound on a subject in need thereof.

In an embodiment, methods of preventing bacterial growth in a subject in need thereof are provided, including preparing a supplemented wound dressing according to the present methods and applying the supplemented wound dressing to a wound on the subject in need thereof. The supplemented wound dressing may inhibit bacterial growth in the wound on the subject in need thereof, including particularly inhibiting the growth of methicillin-resistant *Staphylococcus aureus*.

In an embodiment, the wound dressing used may be waterproof surgical bandages of the Nescare type.

The present subject matter may be better understood by referring to the following Examples.

Example 1

Preparation of Coffee Extracts

The coffee beans were prepared for roasting by washing the beans with tap water, followed by air drying for a period of about wo hours, and roasting at desired temperatures using a Coffee Roaster (940W 5521/22/GY). The roasting conditions are listed in Table 1. In Table 1 *Ca indicates the use of cardamom, while non-Ca indicates that no Cardamom was added. Roasted and unroasted coffee beans were then ground by an AG-36/SI-557 type coffee grinder.

TABLE 1

The conditions and ingredients used in roasting Khulani coffee samples

| Treatment | Cardamom | Medium Roasted Coffee Beans | | Light Roasted Coffee Beans | | Unroasted Coffee Beans | |
|---|---|---|---|---|---|---|---|
| | | *Ca | Non-Ca | *Ca | Non-Ca | *Ca | Non-Ca |
| Roasting Time (min) | N/A | 30 | | 15 | | N/A | |
| Temperature Range | N/A | 230° C. | | 190° C. | | N/A | |
| Weight of ground Coffee per 100 mL Distilled Water | 10 g | 10 g + 2 g | 10 g | 10 g + 2 g | 10 g | 10 g + 2 g | 10 g |
| Boiling Time | | | | 15 minutes | | | |

Traditional Saudi coffee was prepared in the laboratory under sterile environmental conditions to minimize microbial load contamination as much as possible. To prepare the samples without the addition of cardamom, 10 g of roasted (medium roasting and light roasting) and unroasted coffee beans were placed separately in glass bottles and thoroughly mixed with 100 mL of distilled boiling water, then the boiling process continued for 15 minutes. As for the samples to which cardamom was added, they were prepared as follows: mix 100 mL of distilled boiling water with 10 g of roasted (medium roasting and light roasting) and unroasted coffee (each treatment was prepared in separate glass vials). For each treatment separately add 2 g of crushed cardamom using a mortar and the samples were heated to a boil for 15 minutes. In all the processes, there is a mixture of an aqueous extract that includes coffee with different degrees of roasting without the addition of cardamom and another with the addition of cardamom, and all extracts have been treated with ultraviolet radiation according to the method (Rutala, W. A. and Weber, D. J. (2019) 'Disinfection and sterilization in healthcare facilities', Bennett & Brachman's Hospital Infections: Sixth Edition [Preprint], (May). doi:10.1017/9781107153165.009.). The obtained aqueous extracts were then sterilized by exposure to ultraviolet light for ten minutes.

Example 2

Preparation of Wound Dressings Supplemented with Coffee Extracts

Commercial surgical bandages (Nexcare, Poland) with a width of 25 mm and a length of 72 mm were used to produce wound dressings containing the aqueous extracts of Saudi coffee. The extracts were prepared as described in Example 1. In completely sterile conditions, 0.1 mL of the aqueous extract was added to the inner part of the surgical dressings that stick to the wounds. The dressings were allowed to dry completely at room temperature in entirely contamination-free circumstances. The effectiveness of dressings loaded with the aqueous extracts of Saudi coffee were tested against MRSA in vitro study. The loaded dressings' validity and capacity to maintain their effectiveness was tested for a full month.

Example 3

Testing Antibacterial Activity of Coffee Extracts

To test the effectiveness of previous extracts as antibiotic-resistant antibacterial agents, a standard strain of methicillin-resistant *Staphylococcus aureus* (ATCC 43300) bacteria, known simply as MRSA, was used in this investigation. The results of the standard antibiotic sensitivity test using the Vitek-2 system showed that this strain is resistant to the following antibiotics: imipenem, cefoxitin, ampicillin, penicillin G, oxacillin and amoxicillin-alavulanate. Standard methods were followed in the preparation of culture media used for cultivation of bacteria. The bacterial strain was cultivated at least three times before the assay to ensure their activity. The agar well diffusion method using Mueller-Hinton agar (Scharlab, S. L., Spain) was done according to Clinical and Laboratory Standards Institute (CLSI) and Antimicrobial Susceptibility Testing (as reported previously by Hombach, M., et al., 2012. Effects of clinical breakpoint changes in CLSI guidelines 2010/2011 and EUCAST guidelines 2011 on antibiotic susceptibility test reporting of Gram-negative bacilli. Journal of antimicrobial chemotherapy, 67(3), pp. 622-632.). The suspension of MRSA in a sterile saline physiological solution (0.89% table salt) was prepared from 24-hour-old bacterial colonies to obtain an optical density of 0.65 at 600 nm. The surfaces of Mueller-Hinton plates were inoculated with 0.1 mL of MRSA suspension. After that, standard wells with a diameter of 6 mm were drilled using a disposable sterile glass pipette. Saudi coffee preparations were added to the wells at a concentration of 40 mg/mL, the plates were incubated at 37° C. for 24 hours, after which the inhibition zone was recorded around each hole, which indicates the activity of the preparations against the tested bacteria.

A modified process was used to test the Wound Dressing supplemented with coffee extracts. This modification included not etching the surface of the medium (agar) and instead, the preparation-loaded and non-loaded bandages were gently placed on the surface of the medium (agar) on which the bacterial vaccine was spread according to the above-mentioned standard steps. The biological activity of loaded bandages, after the incubation process at 37° C. for 24 hours, was estimated as an inhibition zone that appears around the preparation-loaded bandages and does not appear in non-loaded-bandages. The experiment continued to be repeated weekly for a whole month to make sure that the loaded bandage retains its effectiveness and that the compounds that adhered to it are stable and do not lose their effectiveness over time.

The results confirmed that all the tested extracts, with their combination of water and coffee (roasted and unroasted), with the addition of cardamom or not, have vital efficacy against MRSA. The aqueous mixture of medium roasted coffee without the addition of cardamom was chosen to prepare the surgical dressings loaded with the aqueous extract of Saudi coffee.

It is to be understood that the clinical dressing loaded with coffee extract is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A method of making a supplemented wound dressing consisting of:
   providing coffee beans;
   washing the coffee beans;
   drying the coffee beans;
   roasting the coffee beans at about 230° C. for about 30 minutes;
   grinding the coffee beans;
   mixing about 10 g of the coffee beans with about 100 mL sterile distilled water to obtain an aqueous solution;
   boiling the aqueous solution for about 15 minutes to obtain an extract;
   sterilizing the extract;
   providing a wound dressing;
   adding the sterilized extract to a wound contacting portion of the wound dressing; and
   drying the wound dressing under sterile conditions to obtain the supplemented wound dressing.

2. The method of making a supplemented wound dressing of claim 1, wherein the coffee beans are Khawlani coffee beans.

3. The method of making a supplemented wound dressing of claim 1, wherein the wound dressing inhibits the growth of methicillin-resistant *Staphylococcus aureus*.

4. A method of making a supplemented wound dressing consisting of:
   providing coffee beans;
   washing the coffee beans;
   drying the coffee beans;
   roasting the coffee beans at about 190° C. for about 15 minutes;
   grinding the coffee beans;
   mixing about 10 g of the coffee beans with about 100 mL sterile distilled water to obtain an aqueous solution;
   boiling the aqueous solution for about 15 minutes to obtain an extract;

sterilizing the extract;
providing a wound dressing;
adding the sterilized extract to a wound contacting portion of the wound dressing; and
drying the wound dressing under sterile conditions to obtain the supplemented wound dressing.

5. The method of making a supplemented wound dressing of claim 4, wherein the coffee beans are Khawlani coffee beans.

6. The method of making a supplemented wound dressing of claim 4, wherein the wound dressing inhibits the growth of methicillin-resistant *Staphylococcus aureus*.

7. A method of making a supplemented wound dressing consisting of:
providing coffee beans;
washing the coffee beans;
drying the coffee beans;
grinding the coffee beans;
mixing about 10 g of the coffee beans with about 100 mL sterile distilled water to obtain an aqueous solution;
boiling the aqueous solution for about 15 minutes to obtain an extract;
sterilizing the extract;
providing a wound dressing;
adding the sterilized extract to a wound contacting portion of the wound dressing; and
drying the wound dressing under sterile conditions to obtain the supplemented wound dressing.

8. The method of making a supplemented wound dressing of claim 7, wherein the coffee beans are Khawlani coffee beans.

9. The method of making a supplemented wound dressing of claim 7, wherein the wound dressing inhibits the growth of methicillin-resistant *Staphylococcus aureus*.

* * * * *